(12) United States Patent
Hempel et al.

(10) Patent No.: US 7,787,596 B2
(45) Date of Patent: Aug. 31, 2010

(54) X-RAY ABSORPTION GRID

(75) Inventors: Eckhard Hempel, Fürth (DE); Martin Hoheisel, Erlangen (DE); Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 61 days.

(21) Appl. No.: 12/126,112

(22) Filed: May 23, 2008

(65) Prior Publication Data
US 2008/0317213 A1    Dec. 25, 2008

(30) Foreign Application Priority Data
May 24, 2007    (DE) ................ 10 2007 024 156

(51) Int. Cl.
*G21K 1/00* (2006.01)
(52) U.S. Cl. ............... 378/154; 378/2; 378/145; 378/155
(58) Field of Classification Search ............. 378/2, 378/154
See application file for complete search history.

(56) References Cited

U.S. PATENT DOCUMENTS

| | | | | |
|---|---|---|---|---|
| 4,951,305 A | * | 8/1990 | Moore et al. | 378/147 |
| 6,086,643 A | * | 7/2000 | Clark et al. | 29/623.2 |
| 6,188,032 B1 | * | 2/2001 | Hartman | 206/308.1 |
| 7,646,843 B2 | * | 1/2010 | Popescu et al. | 378/5 |
| 2002/0037070 A1 | * | 3/2002 | Tang | 378/154 |
| 2007/0183579 A1 | | 8/2007 | Baumann et al. | |
| 2007/0183582 A1 | | 8/2007 | Baumann et al. | |

FOREIGN PATENT DOCUMENTS

| | | |
|---|---|---|
| EP | 1 447 046 | 8/2004 |
| EP | 1 731 099 | 12/2006 |

OTHER PUBLICATIONS

"MODULIGA: The LIGA Process as a Modular Production Method- Current Standardization Status in Germany," Hahn et al, Microsystem Technologies, vol. 11 (2005) pp. 240-245.

\* cited by examiner

*Primary Examiner*—Hoon Song
*Assistant Examiner*—Mona M Sanei
(74) *Attorney, Agent, or Firm*—Schiff Hardin LLP

(57) ABSTRACT

An x-ray absorption grid produced by a lithography method for use in a phase-contrast CT system has at least two individual grids arranged atop one another in the radiation direction. Each individual grid has a grid area with a grid structure including grid webs and grid gaps in alternation. Each individual grid has a region outside of the grid area (outer region). The outer region of the at least two individual grids has toothed structures corresponding to one another at least two points. The toothed structures are generated as well in the production of the grid structure. The toothed structures have a position that is defined relative to the grid structure, such that a defined alignment of the individual grids occurs given a combination of the individual grids by engagement of the toothed structures of individual grids lying atop one another.

11 Claims, 4 Drawing Sheets

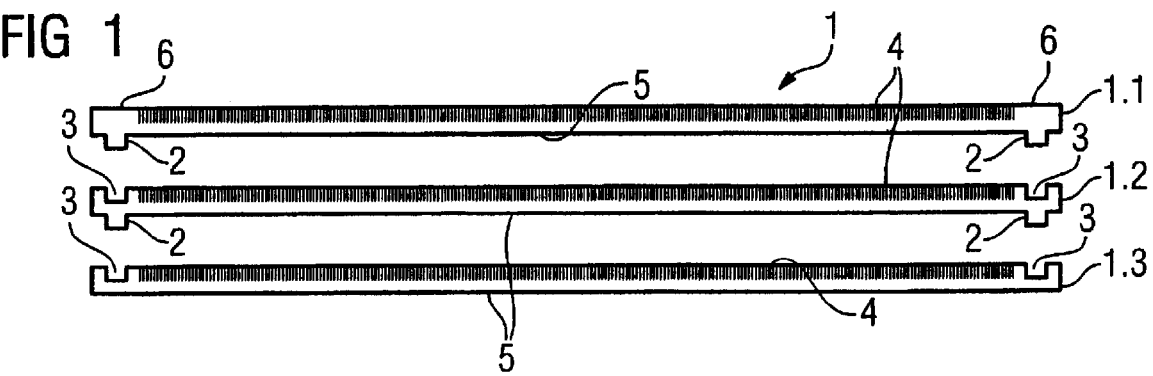
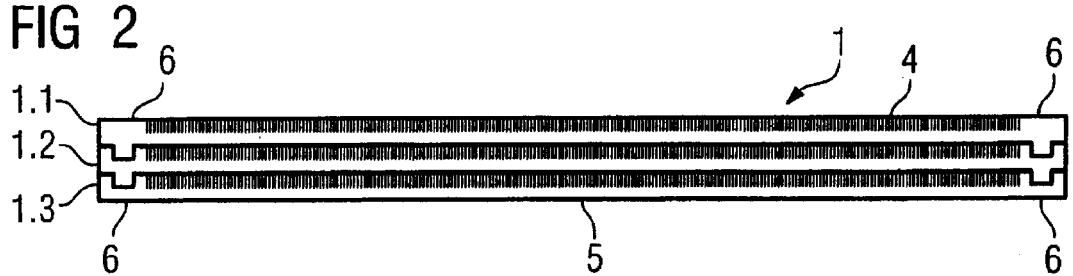
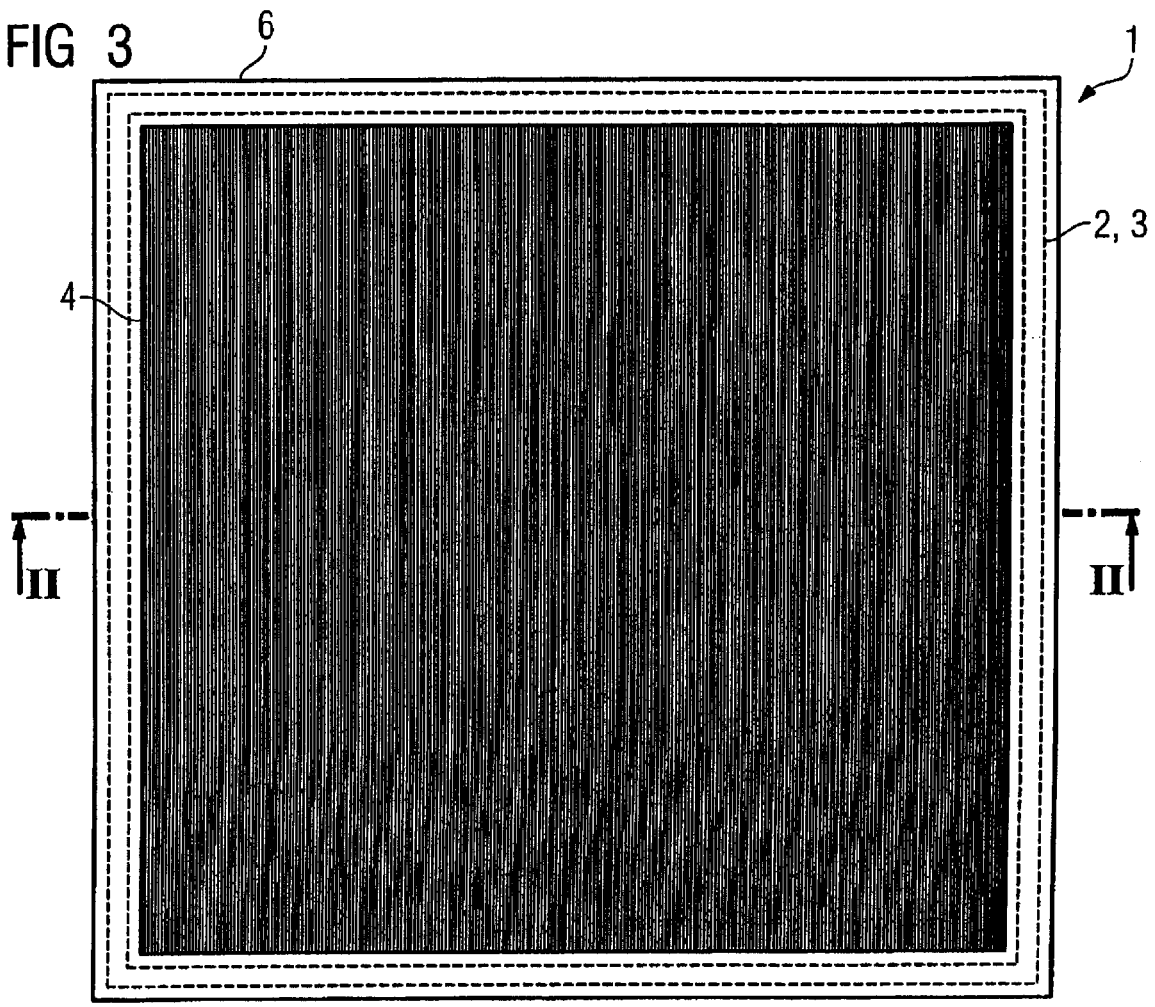

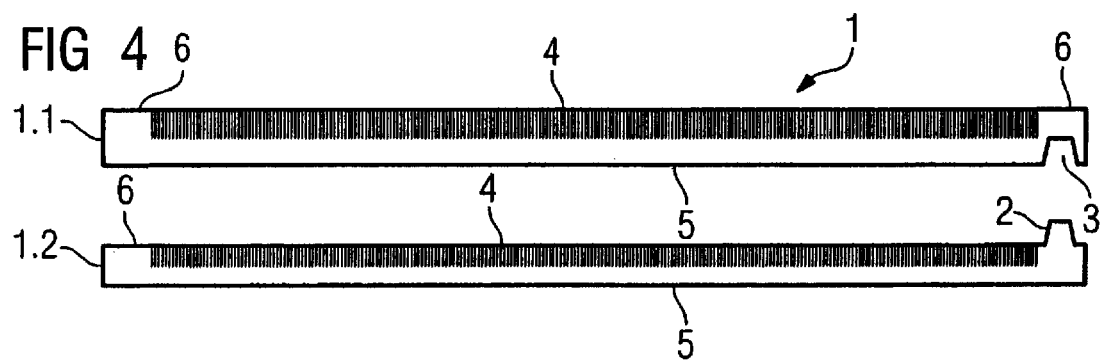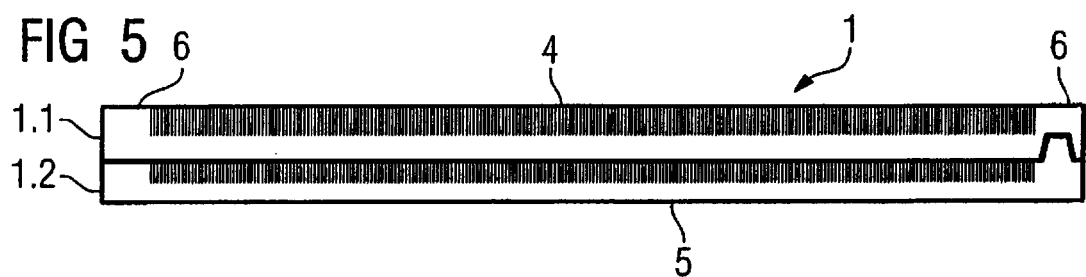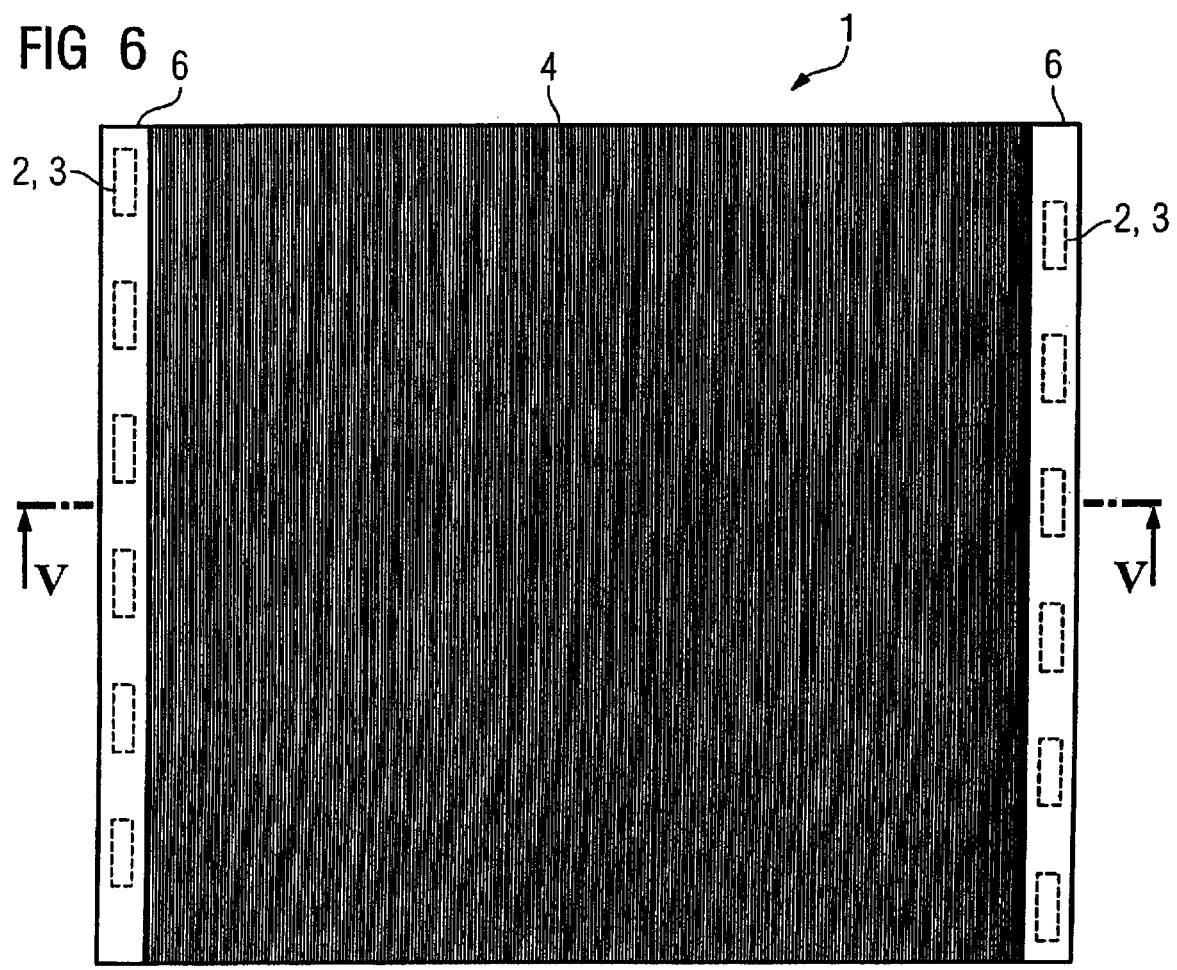

X-RAY ABSORPTION GRID

BACKGROUND OF THE INVENTION

1. Field of the Invention

The present invention concerns an x-ray absorption grid system of the type produced by a lithography method for use in a system for x-ray phase contrast imaging, in particular a phase contrast CT system, wherein the grid system is composed of at least two individual grids arranged atop one another in the radiation propagation direction, with each individual grid having a grid area which exhibits a plurality of grid webs and grid gaps occurring in alternation.

2. Description of the Prior Art and Related Subject Matter

X-ray phase contrast imaging (in particular phase contract CT) is generally known. For example, refer to the patent application EP 1 447 046 A1. A number of x-ray absorption grids are required for this x-ray phase contrast imaging. A focus-side grid is required for generation of quasi-coherent foci, as well as a phase grid for phase modulation of the x-ray radiation by half a wavelength and an amplitude grid are arranged at the detector. The amplitude grid transduces the phase information into measurable intensity signals by step-by-step shifting. Intensity signals can be acquired with the x-ray detector situated behind the amplitude grid.

The design requirements are very demanding, in particular for the detector-side amplitude grid. Structure heights of approximately 50 µm-120 µm given structure widths of approximately 1 µm should be realized over as large an area as possible. A material with maximal absorption properties is necessary for the generation of such x-ray grids; the use of gold as a grid material is proposed for this purpose, for example.

In principle such grids can be produced by nanotechnology such as, for example, the LIGA method, wherein the costs for this rise significantly with the ratio of structure heights to structure widths of the grid. In German patent application DE 10 2006 037 281.6 (not published before the priority date) it is proposed to stack multiple grids atop one another instead of a single grid, and to align said multiple grids such that the grid webs and grid gaps come to lie atop one another in the direction of the x-ray radiation such that, with the use of multiple x-ray grids that can be produced with an advantageous structure height and structure width ratio (for example 40 µm web height and 1-2 µm web and gap widths), a corresponding overall grid can be produced by a number of sub-grids.

For alignment, in the last cited printed document it is proposed to move the grids in the beam path relative to one another and to minimize the Moiré patterns arising due to a possibly present misalignment. For a basic pre-alignment it is proposed to apply diverse markers to the sub-grids so that the basic alignment can orient on these markers.

Although the proposed method can be implemented in principle, it is relatively complicated to execute such a method given an x-ray source located in operation, in particular if not just two grids should be aligned against one another, but rather a number of grids (for example three or four) arranged atop one another are to be aligned.

SUMMARY OF THE INVENTION

An object of the invention is to provide an x-ray absorption grid produced from multiple individual grids such that the alignment of the individual grids can ensue in a simpler manner in the assembly of the entire x-ray grid.

The invention is based on the recognition that it is possible, by appropriate application of toothed structures on the top and bottom of individual grids during the manufacturer process, to assemble these individual grids such that the toothed structures engage with one another and an automatic alignment of the grid structures relative to one another can hereby result in the predetermined manner. No elaborate alignment of the grid structures during an exposure is necessary. Furthermore, in contrast to the previously described method with the Moiré pattern, it is now also possible to already provide an arbitrary arrangement of the grid structures relative to one another in production. For example, not only can a congruent alignment of the sub-grids arranged atop one another be achieved, but there also exists the possibility to merge these sub-grids with one another with a defined offset so that grid structures are also achieved that are functional for an angled irradiation of x-ray radiation.

Based on the above concepts, an x-ray absorption grid is produced by a lithography method (advantageously an x-ray lithography method) for use in an x-ray phase contrast system (advantageously a phase contrast CT system), wherein this x-ray absorption grid has at least two individual grids arranged atop one another in the radiation direction, and each individual grid has a grid area with a number of grid webs and grid gaps occurring in alternation.

The improvement according to the invention is in that each individual grid have a region outside of the grid area (outer region) and the respective outer regions of the at least two individual grids have toothed structures corresponding to one another at least at two points. The toothed structures are generated as well in the production of the grid structure. The toothed structures have a position that is defined relative to the grid structure, such that individual grids lying on one another exhibit a defined alignment of the individual grids via engagement of the toothed structures with one another.

The production of the toothed structures is thus integrated into the process of the grid production, such that it is possible to position these toothed structures precisely relative to the generated grids so that combining multiple sub-grids given simultaneous positive engagement of the toothed structures leads to an optimal alignment of the grids relative to one another. This alignment can thereby be arbitrarily selected. A congruent alignment of the grid structures may be desired, or it can also be required to generate a certain transverse offset of the grids relative to one another in the event that the offset of the x-ray grids ensues in a region in which the x-ray radiation no longer strikes the x-ray absorption grid perpendicularly.

The toothed structure which leads to the relative alignment of the sub-grids relative to one another can be executed, for example, as a positive-negative structure. Examples of this are a cylindrical pin for a round cylindrical hole, an n-edged pin for an n-edged hole or the like. Moreover, the side walls of the toothed structure can also proceed conically for a better engagement.

The outer region can also be a border surrounding the grid area on at least two sides. A particularly secure variant is thereby generated when the outer region is a border surrounding the grid area altogether, thus on four sides.

Moreover, in another embodiment the outer region of the grid area is provided with multiple external tabs distributed around the grid area. The toothed structures can then be integrated into these external tabs.

Furthermore, it is particularly advantageous when the individual grids are adhered to one another such that they form a structure that securely holds together.

With regard to the manufacturing costs, it can additionally be particularly advantageous when, instead of at least two individual grids, at least three or even four individual grids are arranged atop one another. For embodiments in which a transverse offset of the grid is realized in order to also be able to be used for x-ray radiation radiated at an angle, it can be more advantageous to use a higher number of individual grids since the gradations of the individual grids can then turn out to be less severe.

In addition to the arrangement variants of the sub-grids with grid structures arranged congruently atop one another or, grid structures arranged uniformly offset relative to one another, the possibility also exists to arrange a number of individual grids atop one another whose grid period rises in one direction from individual grid to individual grid. For example, a quasi-curved grid can be reproduced by a planar grid, in which quasi-curved grid the grid period is also less towards the radiation center (corresponding the expansion of the radiation) than away from the radiation center.

Furthermore, it is concretely proposed that the individual grids are produced by a LIGA method (lithography, electroplating and molding). This method is, for example, described in L. Hahn et al., Microsystem Technologies 11 (2005) 240-245, "MODULIGA: The LIGA-process as a modular production method-current standardization status in Germany". This LIGA method designates a method which is based on a combination of deep lithography, electroplating and micro-molding. Microstructures with dimensions up to 0.2 µm, structure heights up to 3 mm and aspect ratios up to 50, made of plastic, metal and ceramic materials can be produced with this method. In the present case metals (such as gold, for example) are used for production of the grids in order to achieve an optimally high absorption ratio between the grid webs and grid gaps. In such a LIGA method, initially an x-ray-or UV-sensitive plastic layer (PMMA) up to 1 mm thick is applied on a base plate with an electrically conductive cover layer. A lithographic deep structuring is subsequently generated by means of high-energy radiation, for example by means of parallel synchrotron radiation or (given lesser requirements) by means of mono-energetic UV radiation. The exposed regions are subsequently dissolved away with a suitable developer and metal is incorporated into the structure interstices via a galvanic deposition method. Gold appears to be particularly suitable here as a metal since it generates a high absorption ratio between the grid webs and grid gaps.

BRIEF DESCRIPTION OF THE DRAWINGS

FIG. 1 shows an x-ray absorption grid formed of three sub-grids in accordance with the invention, in an unassembled state.

FIG. 2 shows x-ray absorption grid in accordance with the invention, formed of three sub-grids in an assembled state in cross-section.

FIG. 3 shows the x-ray absorption grid of FIG. 2 in a plan view.

FIG. 4 shows an x-ray absorption grid in accordance with the invention, formed of two sub-grids in an unassembled state.

FIG. 5 shows an x-ray absorption grid in accordance with the invention, formed of two sub-grids in an assembled state.

FIG. 6 shows the x-ray absorption grid of FIG. 5 in plan view.

DESCRIPTION OF THE PREFERRED EMBODIMENTS

Figure 7:
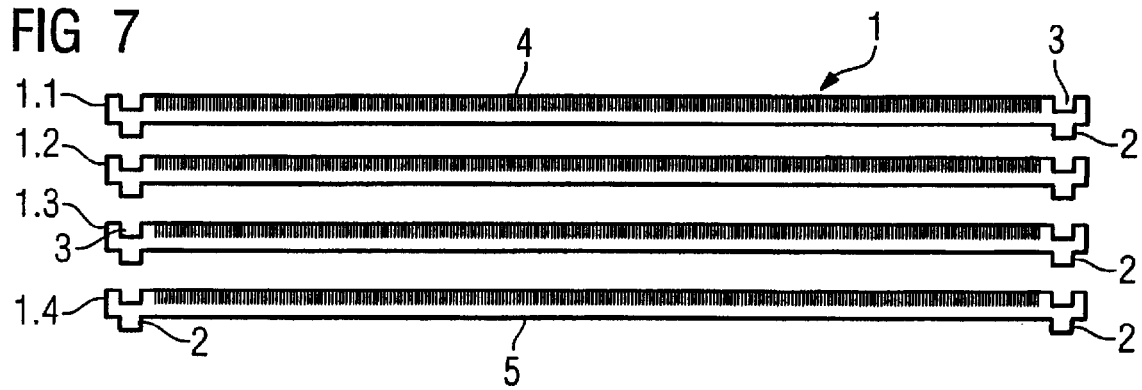
FIG. 7 shows an x-ray absorption grid in accordance with the invention, formed of four sub-grids in an unassembled state.

A first version of an inventive x-ray absorption grid which consists of the three sub-grids 1.1, 1.2 and 1.3 is shown in FIG. 1. The sub-grids have a substrate 5 uniformly distributed over the entire area of the grid, on which substrate 5 the grid webs and the grid gaps are arranged that all together form the grid area 4. The substrate 5 runs on the side in an outer region 6 in which a grid structure is no longer located, wherein toothed elements 2 that can engage in opposite gaps 3 of the adjacent grid are arranged in this outer region, however.

If the sub-grids 1.1, 1.2 and 1.3 are assembled, the x-ray absorption grid 1 shown in FIG. 2 in section A-A results with the individual grids 1.1, 1.2 and 1.3 that are aligned relative to one another in the desired manner due to the mutual engagement of the toothed structures, such that a further adjustment can be omitted.

The x-ray absorption grid 1 is again shown in FIG. 3 in plan view. Here the centrally arranged grid area 4 with the grid webs and grid gaps is recognizable. The grid area 4 is circumferentially enclosed on four sides by an outer region 6 in which the toothed structure 2/3 is likewise circumferentially arranged.

Three sub-grids 1.1, 1.2 and 1.3 that are different with regard to their toothed structure are used in the x-ray absorption grid shown here in FIGS. 1 through 3. As can be seen from FIGS. 1 and 2, the upper individual grid 1.1 has a toothed structure 2 only on the underside while the lower individual grid 1.3 has a toothed gap 3 only on its top side. The middle grid 1.2 possesses a toothed gap 3 on the top side and a toothed structure 2 on the underside of the outer region, such that after an assembly of these three sub-grids (as shown in FIG. 2) an entire x-ray absorption grid appears which no longer possesses toothed structures facing outwards.

FIGS. 4, 5 and 6 show a further version of an x-ray absorption grid that is formed only of two individual grids 1.1 and 1.2. In this embodiment of the x-ray absorption grid the outer region 6 runs only on two opposing sides. Moreover, no continuous toothed structure is shown in the outer region; rather, individual gaps 3 and projections 2 engaging in them are apparent that (as is clear from FIG. 6) are arranged offset relative to one another, for example. The toothed structures additionally possess a slightly conical shape, such that the assembly of the individual grids 1.1 and 1.2 is made easier. The same effect as given the circumferential toothed structure is achieved in the two outer regions 6 due to the repeatedly divided toothed structures, namely that the grids can gradient echo securely assembled both in the grid line longitudinal direction and in the transverse direction and a slippage is prevented.

Figure 8:
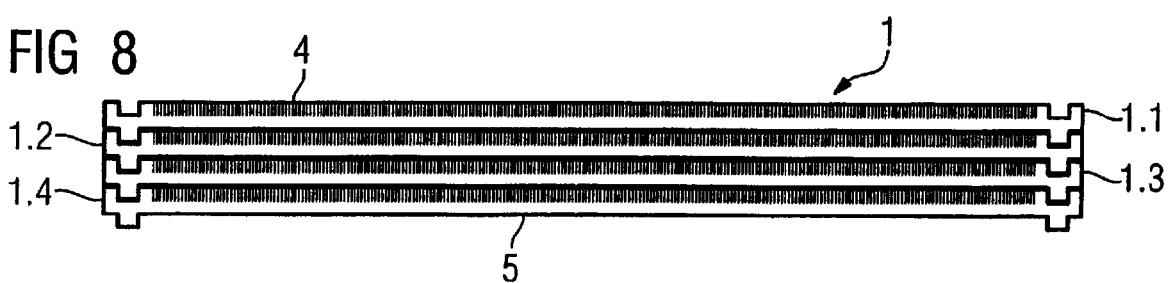
FIG. 8 shows the x-ray absorption grid of FIG. 7 in an assembled state.
Figure 9:
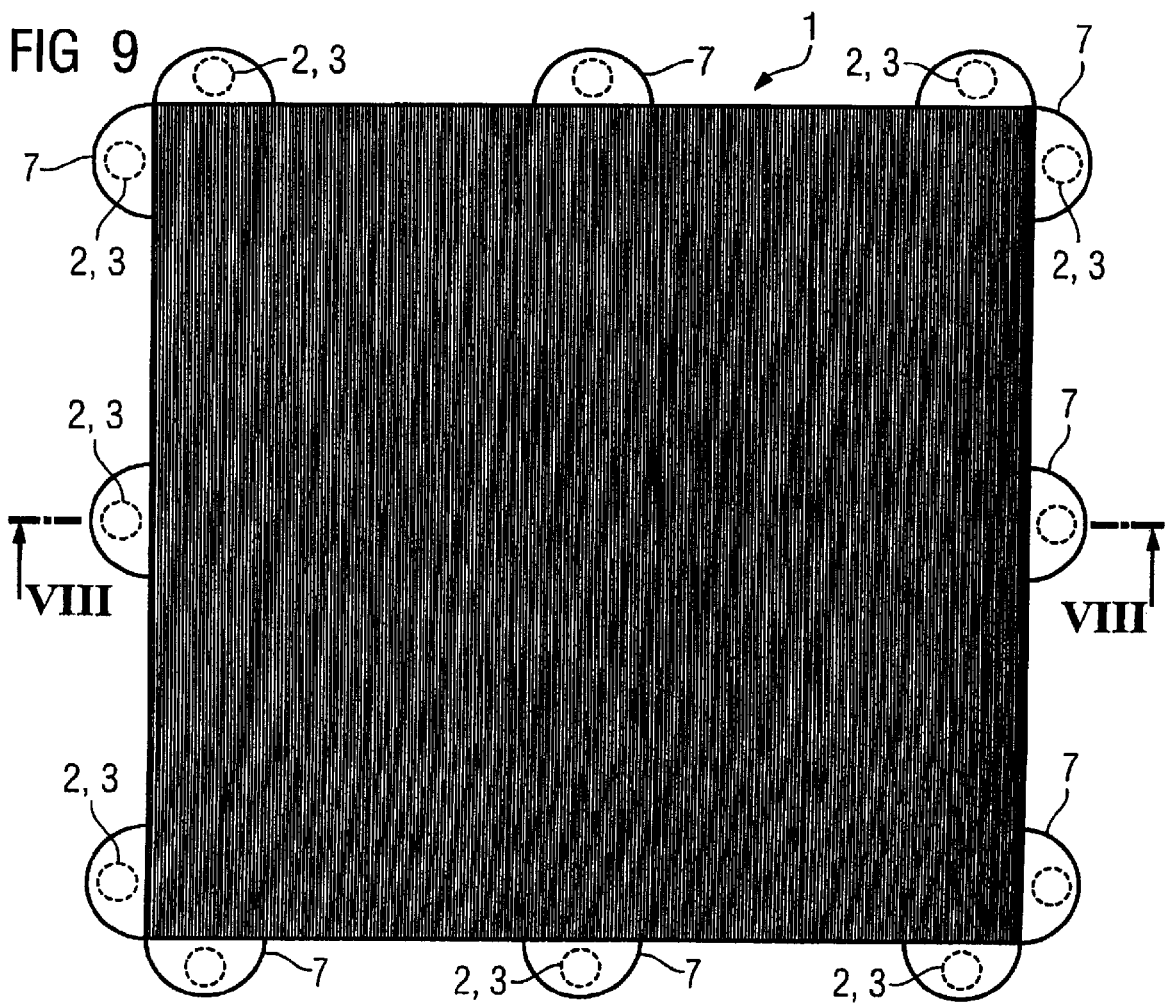
FIG. 9 shows the x-ray absorption grid of FIG. 8 in plan view.

A further embodiment of an inventive x-ray absorption grid is shown in FIGS. 7, 8 and 9. This has four individual grids 1.1 through 1.4. In this case all grids 1.1 through 1.4 are designed identically (at least with regard to their outer region, which here is formed from individual external tabs), and both the positive and the negative toothed structures 2 and 3 that engage in one another and therefore ensure the relative positioning of the individual grids 1.1 through 1.4 relative to one another are located in each external tab 7.

Figure 10:
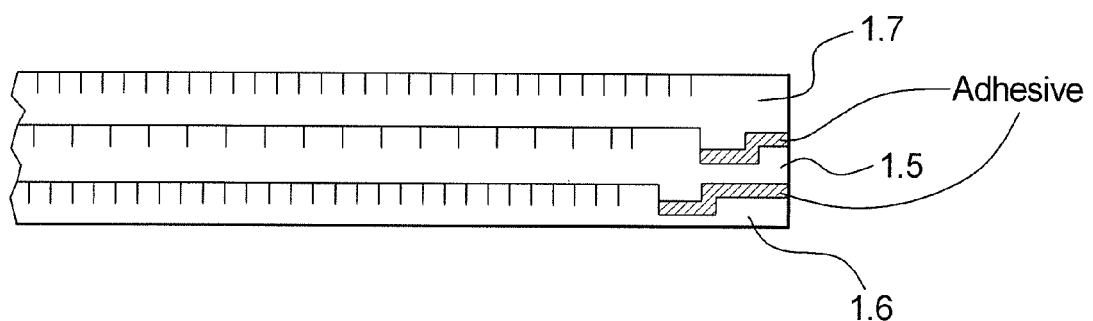
FIG. 10 is a fragmentary side view of a further embodiment of the x-ray absorption grid in accordance with the invention.

FIG. 10 shows a portion of a further embodiment of the x-ray absorption grid in a side view, which has the same individual grid 1.1 as shown in the previous figures, but modified versions of the other grids 1.5 and 1.6. In the embodiment of FIG. 10, the toothed structures are offset from each other, so that the grid structures in the respective individual grids 1.1 and 1.6 are also offset relative to each other.

As also schematically indicated in FIG. 10, the grid structure in the individual grid 1.5 has a different periodicity from the grid structures of the individual grids 1.1 and 1.6, as schematically illustrated by a larger spacing between the lines indicating the grid walls.

As also shown in FIG. 10, the respective grids can be held together by an adhesive (shown exaggerated in FIG. 10) between adjacent individual grids.

Furthermore, by means of the toothed structures on the outsides after the assembly of the four individual grids, the possibility exists to likewise use these toothed structures as a positioning aid upon assembly with the detector, for example, in that corresponding counter-structures exist in the region of the detector structure.

Although modifications and changes may be suggested by those skilled in the art, it is the intention of the inventor to embody within the patent warranted hereon all changes and modifications as reasonably and properly come within the scope of his contribution to the art.

We claim as our invention:

1. An x-ray absorption grid system comprising:
   at least two individual grids each produced by a lithography technique, said at least two individual grids being arranged atop one another in a direction of radiation propagation therethrough to form a grid combination, and each individual grid comprising a substrate with no gaps therein and a grid area on said substrate exhibiting a grid structure formed on said substrate with said substrate remaining beneath said grid structure, said grid structure comprising a plurality of radiation-absorbing grid webs and grid gaps in alternation;
   the substrate of each individual grid also comprising an outer region that extends outside of said grid area;
   the respective outer regions of the substrate of each of said at least two individual grids comprising toothed structures corresponding to one another at at least two points, said toothed structures being generated in the same lithography technique used to produce the grid structure;
   said toothed structures being located on the outer region of the substrate of each of said at least two individual grids at a defined position relative to the grid structure on that substrate, to produce a defined alignment of the respective individual grids relative to each other in said grid combination by engagement of the toothed structures of the respective individual grids atop one another; and
   the respective grid structures of said at least two individual grids, and said defined position and said defined alignment being structured relative to each other to set an interaction of said respective grid structures with said radiation propagating through said respective grid structures that produces a radiation beam exiting said grid combination that has beam characteristics for phase-contrast CT.

2. An x-ray absorption grid system as claimed in claim 1 wherein at least one of said toothed structures is a positive-negative structure.

3. An x-ray absorption grid system as claimed in claim 1 wherein said outer region in each of said individual grids forms a border at least partially surrounding the grid area thereof.

4. An x-ray absorption grid system as claimed in claim 1 wherein said outer region of each of said individual grids completely surrounds the grid area thereof.

5. An x-ray absorption grid system as claimed in claim 1 wherein said outer region of each of said individual grids comprises multiple external tabs distributed around said grid area, at which said toothed structures are carried.

6. An x-ray absorption grid system as claimed in claim 1 comprising adhesive that adheres said individual grids with one another in said grid combination.

7. An x-ray absorption grid system as claimed in claim 1 comprising at least three of said individual grids arranged atop one another in said combination.

8. An x-ray absorption grid system as claimed in claim 1 wherein the respective toothed structures are positioned to cause all of the individual grids in said grid combination to be congruent with each other with regard to said grid webs and said grid gaps.

9. An x-ray absorption grid system as claimed in claim 1 wherein said toothed structures are positioned on respective individual grids to cause the respective individual grids atop one another in said grid combination to exhibit a defined offset relative to the grid webs and the grid gaps, said offset being perpendicular to a longitudinal direction of said grid webs.

10. An x-ray absorption grid system as claimed in claim 1 wherein said individual grids in said grid combination have respectively different grid periodicities.

11. An x-ray absorption grid system as claimed in claim 1 wherein said individual grids are produced with a LIGA method.

* * * * *